United States Patent [19]

Guyon

[11] Patent Number: 5,625,066

[45] Date of Patent: Apr. 29, 1997

[54] OPTICALLY ACTIVE HYDROQUININE (AMINO-3 PHENYL)-1 ETHANESULFONATE, PREPARATION AND USE THEREOF

[75] Inventor: Claude Guyon, Saint Maur des Fosses, France

[73] Assignee: Rhone-Poulenc Rorer S.A., Antony, France

[21] Appl. No.: 397,046

[22] PCT Filed: Sep. 6, 1993

[86] PCT No.: PCT/FR93/00848

§ 371 Date: Mar. 10, 1995

§ 102(e) Date: Mar. 10, 1995

[87] PCT Pub. No.: WO94/06792

PCT Pub. Date: Mar. 31, 1994

[30] Foreign Application Priority Data

Sep. 11, 1992 [FR] France ................ 92 10839

[51] Int. Cl.$^6$ ............... C07D 403/06; C07D 453/04
[52] U.S. Cl. ................................ 546/134
[58] Field of Search ............................ 546/134

[56] References Cited

U.S. PATENT DOCUMENTS

| | | | |
|---|---|---|---|
| 5,093,498 | 3/1992 | Dolling et al. | 546/134 |
| 5,162,339 | 11/1992 | Lowe, III | 514/305 |

*Primary Examiner*—Alan L. Rotman
*Attorney, Agent, or Firm*—Finnegan, Henderson, Farabow, Garrett & Dunner, L.L.P.

[57] ABSTRACT

This invention relates to an optically active hydroquinine (amino-3 phenyl)-1 ethanesulfonate (form A), preparation thereof and its use as an intermediate in the preparation of cholecystokinine and gastrin antagonists.

5 Claims, No Drawings

OPTICALLY ACTIVE HYDROQUININE (AMINO-3 PHENYL)-1 ETHANESULFONATE, PREPARATION AND USE THEREOF

CROSS-REFERENCE

This application is a 371 of PCT/FR 93/00848.

DESCRIPTION OF THE INVENTION

The present invention relates to optically active hydroquinine 1-(3-aminophenyl)ethanesulphonate (Form A), its preparation and its use as intermediate in the preparation of enantiomers which can be used as antagonists of cholecystokinin and of gastrin.

Hydroquinine 1-(3-aminophenyl)ethanesulphonate (Form A) can be prepared by the following process:

a) action of an alkali metal sulphite on (RS)-1-(1-bromoethyl)-3-nitrobenzene and conversion to the potassium salt to obtain (RS)-potassium 1-(3-nitrophenyl)ethanesulphonate, b) conversion of (RS)-potassium 1-(3-nitrophenyl) ethanesulphonate to benzylquininium 1-(3-nitrophenyl)ethanesulphonate and isolation of Form A, c) reduction of form A benzylquininium 1-(3-nitrophenyl)ethanesulphonate.

It is particularly advantageous to perform stage a) in aqueous medium at a temperature of between 50° C. and 100° C. and preferably at 80° C.

The alkali metal sulphite is preferably sodium or potassium sulphite.

To recover the product, it is preferable to convert it into tetraalkylammonium or trialkylphenylalkylammonium salt, to isolate it and then to convert it back into the potassium salt form.

Stage b) is performed by means of an N-benzylquininium halide and especially the chloride, in the presence of potassium dihydrogenphosphate, in aqueous medium, at a temperature of between 10° and 30° C. and preferably of 20° C.

The reduction in stage c) is generally performed by means of hydrogen under pressure, in the presence of a catalyst such as palladium, at a temperature of between 10° C. and 30° C. The hydrogen is generally employed at a pressure of 100 kPa.

(RS)-1-(1-Bromoethyl)-3-nitrobenzene can be prepared by the method described by E. Felder et al., J. Med. Chem., 13, 559 (1970).

Hydroquinine 1-(3-aminophenyl)ethanesulphonate (Form A) is of particular interest as intermediate for the preparation of the enantiomers of the compounds of formula:

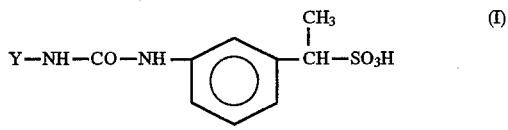

(I)

in which Y denotes:

A) a —$CH_2$—CO—$NR_1R_2$ residue in which $R_1$ denotes a radical which is (a) phenyl optionally substituted by one or more substituents chosen from halogen atoms and alkyl, alkoxy, hydroxyl polyfluoroalkyl, nitro, alkylthio, alkoxycarbonyl, carboxyl, acylamino, methylenedioxy, polyfluoroalkoxy, trifluoromethylthio, phenoxy, phenyl, benzyl, phenylamino and CONR$_3$R$_4$ radicals in which $R_3$ and $R_4$, which are identical or different, denote a hydrogen atom, an alkyl, phenyl (optionally substituted by one or more substituents chosen from halogen atoms and alkyl, alkoxy and alkylthio radicals), indanyl, cycloalkylalkyl, cycloalkyl or phenylalkyl radical or else $R_3$ and $R_4$ together with the nitrogen atom to which they are attached form a saturated or unsaturated mono- or polycyclic heterocyclic ring containing 4 to 9 carbon atoms and 1 or more heteroatoms (O, N, S) and optionally substituted by one several alkyl, alkoxy, alkoxycarbonyl, dialkylcarbamoyl or phenyl radicals or in combination with a carbon atom of the heterocyclic ring by a 4- or 5-membered spiromonocyclic ring optionally containing one several heteroatoms (O, S, N); (b) pyridyl, (c) isoquinolyl, (d) quinolyl, (e) quinoxalinyl (these heterocyclic rings being optionally substituted by one or more substituents chosen from alkyl and phenyl radicals and halogen atoms), (f) alkyl, (g) phenylalkyl, (h) naphthyl, (i) 5,6,7,8-tetrahydronaphthyl, (j) 1,2,3,4-tetrahydronaphthyl, (k) alkoxycarbonylalkyl or (l) cycloalkyl, $R_2$ denotes a —CH($R_5$)—CO—$R_6$ chain in which $R_5$ denotes a hydrogen atom or an alkyl, alkoxycarbonyl or phenyl radical (optionally substituted by one or more substituents chosen from halogen atoms and alkyl, alkoxy, alkylthio, nitro and amino radicals) and $R_6$ denotes an alkoxy, cycloalkyloxy (optionally substituted by at least one alkyl radical), cycloalkylalkyloxy, phenylalkyloxy, polyfluoroalkyloxy, cinnamyloxy and —$NR_3R_4$ radical, B) a residue of the formula:

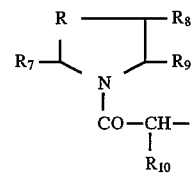

in which:

either R denotes a methylene, ethylene, SO, $SO_2$ or CHOH radical or a sulphur atom, $R_7$ denotes a pyridyl radical optionally substituted by one or more alkyl radicals, furyl optionally substituted by one or more alkyl radicals, thienyl optionally substituted by one or more alkyl radicals, quinolyl optionally substituted by one or more alkyl radicals, naphthyl optionally substituted by one or more alkyl radicals, indolyl optionally substituted by one or more alkyl radicals or phenyl optionally substituted by one or more substituents chosen from halogen atoms and alkyl, alkoxy, hydroxyl, nitro, amino, monoalkylamino, dialkylamino, alkoxycarbonyl, —CO—$NR_{11}R_{12}$, —NH—CO—$CH_3$, trifluoromethyl or trifluoromethoxy radicals and $R_8$ denotes a hydrogen atom, or R denotes a methylene radical, $R_7$ denotes a hydrogen atom and $R_8$ denotes a phenyl radical, or R denotes a radical $CHR_{13}$, each of $R_7$ and $R_8$ denotes a hydrogen atom, $R_9$ denotes an alkoxycarbonyl, cycloalkyloxycarbonyl, cycloalkylalkyloxycarbonyl, —$CONR_{14}R_{15}$ or phenyl radical optionally substituted by one or more substituents chosen from alkyl, alkoxy or hydroxyl radicals, $R_{10}$ denotes a hydrogen atom or an alkyl radical, $R_{13}$ denotes a phenyl radical, $R_{11}$ denotes a hydrogen atom or an alkyl, phenylalkyl or phenyl radical optionally substituted by one or more substituents chosen from halogen atoms and alkyl, alkoxy and alkylthio radicals, $R_{12}$ denotes an alkyl, phenylalkyl or phenyl radical optionally substituted by one or more substituents chosen from halogen atoms and alkyl, alkoxy and alkylthio radicals, or else $R_{11}$ and $R_{12}$ with the nitrogen atom to which they are attached form a saturated or unsaturated mono- or polycyclic heterocyclic ring containing 4 to 9 carbon atoms and one or more heteroatoms (O, N) and optionally substituted by one or more alkyl radicals, $R_{14}$ denotes a hydrogen atom or an alkyl, cycloalkylalkyl, cycloalkyl, phenylalkyl or phenyl radical optionally substituted by one or more substituents chosen from halogen atoms and alkyl, alkoxy and alkylthio radicals, $R_{15}$ denotes an alkyl, cycloalkylalkyl, cycloalkyl, phenylalkyl or phenyl radical optionally substituted by one or more substituents chosen from halogen atoms and alkyl, alkoxy and alkylthio radicals, or else $R_{14}$ and $R_{15}$ together with the nitrogen atom to which they are attached form a saturated or unsaturated mono- or polycyclic heterocyclic ring containing 4 to 9 carbon atoms and one or more heteroatoms (O, N, S) and optionally substituted by one or more alkyl radicals, C) a residue of formula:

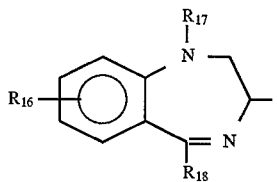

in which:

$R_{16}$ denotes a hydrogen or halogen atom or an alkyl, alkylthio, nitro, hydroxyl or cyano radical, $R_{17}$ denotes an alkyl radical or a —CH($R_5$)—CO—$R_6$ residue, $R_{18}$ denotes a pyridyl or phenyl radical optionally substituted by one or more substituents chosen from halogen atoms and alkyl, alkoxy, hydroxyl, carboxyl, and nitro radicals.

In these definitions the alkyl and alkoxy radicals and the alkyl and alkoxy moieties preferably contain 1 to 4 carbon atoms in a straight or branched chain, the cycloalkyl radicals and moieties 3 to 6 carbon atoms and the acyl radicals 2 to 4 carbon atoms.

These compounds are described in patent applications WO 91/12264, WO 91/13907, WO 91/13874, FR 9108675 and FR 91124871 as antagonists of cholecystokinin and of gastrin.

The compounds of the formula (I) can be prepared from hydroquinine 1-(3-aminophenyl)ethanesulphonate form A by proceeding as follows:

hydroquinine 1-(3-aminophenyl)ethanesulphonate form A is reacted with a derivative of formula:

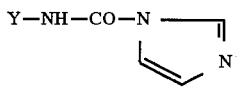

in which Y has the same meanings as in formula (I).

This reaction is generally performed in an inert solvent such as tetrahydrofuran or dimethylformamide, a chlorinated solvent or an aromatic-solvent (for example benzene or toluene) at a temperature of between 20° C. and the boiling temperature of the solvent.

The derivatives of formula (II) can be prepared by the processes described in patent applications WO 91/12264, WO 91/13907, WO 91/13874, FR 9108675 and FR 9112481.

EXAMPLES

EXAMPLE 1 a) (RS)-potassium 1-(3-nitrophenyl)ethanesulphonate:

25.3 g of (RS)-1-(1-bromoethyl)-3-nitrobenzene are added to a solution of 20.8 g of sodium sulphite in 260 cm³ of water. The reaction mixture is stirred at 80° C. for 5 hours, cooled to approximately 25° C. and poured into 2.5 liters of a 0.5M aqueous solution of potassium dihydrogenphosphate. 40 g of tetra-n-butylammonium hydrogensulphate are added. The mixture is extracted with 3 times 500 cm³ of methylene chloride. The combined organic phases are washed with 2 times 500 cm³ of water, are dried over magnesium sulphate and are concentrated to dryness at reduced pressure (2.7 kPa) at 40° C. The oil obtained is dissolved in 65 cm³ of acetone, and 34 g of potassium nonafluorobutanesulphonate in solution in 75 cm³ of acetone are added. The insoluble product is separated off by filtration, washed with 3 times 50 cm³ of diisopropyl ether and dried in air. 22.4 g of (RS)-potassium 1-(3-nitrophenyl) ethanesulphonate, melting at a temperature above 260° C., are thus obtained and employed as such in the subsequent syntheses.

NMR spectrum: (200 MHz; DMSO-d) δ (ppm):
1.50 [d, J=7 Hz, 3H: —CH(C$\underline{H}_3$)—]
3.93 [q, J=7 Hz, 1H: —C$\underline{H}$(CH$_3$)—]
7.59 [t, J=8 Hz, 1H: —C$_6$H$_4$(—$\underline{H}$5)]
7.83 [d, J=8 Hz, 1H: —C$_6$H$_4$(—$\underline{H}$6)]
8.10 [broad d, J=8 Hz, 1H: —C$_6$H$_4$(—$\underline{H}$4)]
8.26 [broad s, 1H: —C$_6$H$_4$(—$\underline{H}$2)].

(RS)-1-(1-Bromoethyl)-3-nitrobenzene can be prepared by the method described by E. Felder et al., J. Med. Chem., 13, 559 (1970).

b) N-Benzylquininium 1-(3-nitrophenyl) ethanesulphonate, form A:

87 g of potassium dihydrogenphosphate and 32.4 g of N-benzylquininium chloride are added to a solution of 17.2 g of (RS)-potassium 1-(3-nitrophenyl)ethanesulphonate in 400 cm³ of water. The mixture is extracted with 2 times 300 cm³ of methylene chloride. The combined organic phases are washed with 2 times 200 cm³ of water, are dried over magnesium sulphate and are concentrated to dryness at reduced pressure (2.7 kPa) at 40° C. The solid foam obtained is dissolved in 120 cm³ of 2-propanol at reflux. After cooling, the crystals are separated off by filtration and washed with 2 times 15 cm³ of 2-propanol. After 2 recrystallizations from 350, then 500 cm³ of 2-propanol, 15.6 g of N-benzylquininium 1-(3-nitrophenyl) ethanesulphonate, form A, melting at about 110° C., are obtained; $[\alpha]_D^{20}$=−151.3°±1.5 (C=1.009%; methanol).

c) Hydroquinine 1-(3-aminophenyl)ethanesulphonate, form A:

1.0 g of palladium on black at a concentration of 5% is added to a solution of 10.4 g of N-benzylquininium 1-(3-nitrophenyl)ethanesulphonate, form A, in 350 cm³ of ethanol. The suspension is shaken for 2 hours at a temperature close to 25° C. under hydrogen atmosphere from 1.65 to 2.10 [mt, 4H: 1H of —C$\underline{H}_2$— at 5, 1H of —C$\underline{H}_2$— at 3, >C$\underline{H}$ at 4, >C$\underline{H}$ at 8 of (Q)] from 2.40 to 2.75 [mt, 2H: 1H of >N—(C$\underline{H}_2$—) at 6 and 1H of >N—(C$\underline{H}_2$—) at 7 of (Q)]
3.15 [mt, 1H: 1H of >N—(C$\underline{H}_2$—) at 7 of (Q)]
3.32 [mt, 1H: C$\underline{H}$ at 2 of (Q)]
3.48 [mt, 1H: 1H of >N—(C$\underline{H}_2$—) at 6 of (Q)]
3.99 [s, 3H: —OC$\underline{H}_3$ of (Q)]
4.04 [q, J=7 Hz, 1H: —C$\underline{H}$(CH$_3$)—]
5.69 [s, 1H: —O—C(H)< at 9 of (Q)]
6.48 [mt, 1H: —C$_6$H$_4$ (—$\underline{H}$4)]
6.93 [mt, 2H: —C$_6$H$_4$ (—$\underline{H}$6) and (—$\underline{H}$5)]
7.00 [broad, 1H: —C$_6$H$_4$ (—$\underline{H}$2)]
7.17 [d, J=2 Hz, 1H: (−$\underline{H}$5') of (Q)]
7.31 [dd, J=8.5 and 2.5 Hz, 1H: (−$\underline{H}$7') of (Q)]

7.62 [d, J=5 Hz, 1H: (—H3') of (Q)]
7.96 [d, J=8.5 Hz, 1H: (—H8') of (Q)]
8.70 [d, J=5 Hz, 1H: (—H2') of (Q)]

EXAMPLE OF APPLICATION 7.7 g of hydroquinine 1-(3-aminophenyl) ethanesulphonate, form A, in solution in 45 cm³ of dimethylformamide, are added to a solution of 5.3 g of 2-{2-[(1-imidazolyl)carboxamido]-N-(3-methoxyphenyl) acetamido}-N-methyl-N-phenylacetamide in 360 cm³ of toluene. The reaction mixture is stirred at reflux for 5 hours, cooled to approximately 25° C. and poured into 400 cm³ of water. The pH is adjusted to 8 with a 4N aqueous sodium hydroxide solution. The aqueous solution is washed with 3 times 300 cm³ of ethyl acetate and then 30 g of potassium dihydrogenphosphate and 4.6 g of tetra-n-butylammonium hydrogensulphate are added. The mixture is extracted with 3 times 150 cm³ of methylene chloride. The combined organic phases are dried over magnesium sulphate and concentrated to dryness at reduced pressure (2.7 kPa) at 40° C. The crude product obtained is stirred for 30 minutes in 100 cm³ of diisopropyl ether. The insoluble product is separated off by filtration and then dissolved in 10 cm³ of acetone. 2.6 g of potassium nonafluorobutanesulphonate in solution in 6 cm³ of acetone are added, followed by 5 cm³ of diisopropyl ether. The insoluble resin is separated off and then stirred for 2 hours in 25 cm³ of a mixture of acetone and diisopropyl ether (60/40 by volume). The insoluble product is separated off by filtration, from 7.30 to 7.50 (mt, 11H: aromatics).

8.80 (broad s, 1H: —CO—NH—Ar).

2-{2-[(1-Imidazolyl)carboxamido]-N-(3-methoxyphenyl) acetamido}-N-methyl-N-phenylacetamide can be prepared as follows: a solution of 3.1 g of 2-[2-amino-N-(3-methoxyphenyl)acetamido]-N-methyl-N-phenylacetamide in 30 cm³ of anhydrous tetrahydrofuran is added to a solution of 3.0 g of N,N'-diimidazolecarbonyl in 30 cm³ of anhydrous tetrahydrofuran. The soluton is stirred for 16 hours at a temperature close to 25° C. and then concentrated to dryness at reduced pressure (2.7 kPa) at 40° C. The residue is dissolved in 50 cm³ of ethyl acetate and the solution obtained is washed with 4 times 30 cm³ of water. The organic phase is dried over magnesium sulphate and then concentrated to dryness at reduced pressure (2.7 kPa) at 40° C. After recrystallization from ethyl acetate 3.5 g of 2-{2-[(1-imidazolyl)carboxamido]-N-(3-methoxyphenyl) acetamido}-N-methyl-N-phenylacetamide, melting at 146° C., are obtained.

2-[2-Amino-N-(3-methoxyphenyl)acetamido]-N-methyl-N-phenylacetamide can be prepared as follows: 1.3 g of hydrazine hydrate are added to a solution of 5.5 g of 2-[N-(3-methoxyphenyl)-2-phthalimidoacetamido]-N-methyl-N-phenylacetamide in 60 cm³ of methanol. The reaction mixture is stirred at reflux for 30 minutes and, after cooling, 100 cm³ of water are added. The mixture is concentrated to approximately 100 cm³ and then adjusted to pH 9 with a 2N aqueous sodium hydroxide solution and extracted with 2 times 50 cm³ of ethyl acetate. The combined organic phases are washed with 2 times 50 cm³ of water, are dried over magnesium sulphate and are then concentrated to dryness at reduced pressure (2.7 kPa) at 40° C. 3.0 g of 2-[2-amino-N-(3-methoxyphenyl)acetamido]-N-methyl-N-phenylacetamide are thus obtained in the form of an oil, employed as such in the subsequent syntheses.

2-[N-(3-Methoxyphenyl)-2-phthalimidoacetamido]-N-methyl-N-phenylacetamide can be prepared as follows: 10 cm³ of dimethylformamide are added to a suspension of 80.6 g of 2-[N-(3-methoxyphenyl)-2-phthalimidoacetamido] acetic acid in 900 cm³ of 1,2-dichloroethane, followed by 30.2 g of oxalyl dichloride over an hour. The mixture is stirred for 2 hours at a temperature close to 25° C. and then 58.6 g of N-methylaniline are added over 45 minutes. The reaction mixture is stirred for 2 hours at a temperature close to 25° C., washed with 2 times 500 cm³ of water and then 300 cm³ of a saturated aqueous solution of sodium hydrogencarbonate, is dried over magnesium sulphate and is concentrated to dryness at reduced pressure (2.7 kPa) at 40° C. The residue is stirred for one hour in 300 cm³ of diisopropyl ether, the insoluble product is separated off by filtration, washed with 3 times 60 cm³ of diisopropyl ether and dried in air. 84 g of 2-[N-(3-methoxyphenyl)-2-phthalimidoacetamido]-N-methyl-N-phenylacetamide, melting at 137° C., are thus obtained.

2-[N-(3-Methoxyphenyl)-2-phthalimidoacetamido]acetic acid can be prepared as follows: 74.0 g of trifluoroacetic acid are added to a solution of 42.0 g of tert-butyl 2-[N-(3-methoxyphenyl)-2-phthalimidoacetamido]acetate in 500 cm³ of methylene chloride. The solution obtained is stirred at reflux for 5 hours and then concentrated to dryness at reduced pressure (2.7 kPa) at 40° C. The residue is stirred for one hour in 100 cm³ of diisopropyl ether, the insoluble product is separated off by filtration, washed with 3 times 40 cm³ of diisopropyl ether and dried in air. 36 g of 2-[N-(3-methoxyphenyl)-2-phthalimidoacetamido]acetic acid, melting at 203° C., are thus obtained.

tert-Butyl 2-[N-(3-methoxyphenyl)-2-phthalimidoacetamido]acetate can be prepared as follows: 14.9 g of an oily suspension (60% by weight) of sodium hydride are added over 30 minutes to a solution of 96 g of N-(3-methoxyphenyl)-2-phthalimidoacetamide in 1000 cm³ of anhydrous tetrahydrofuran. The suspension is stirred for 4 hours at a temperature close to 20° C. and then 72.7 g of tert-butyl bromoacetate are added over 15 minutes. The reaction mixture is stirred for 16 hours at a temperature close to 25° C., hydrolysed slowly with 50 cm³ of water and then concentrated to dryness at reduced pressure. The residue obtained is stirred for one hour in 400 cm³ of water, the insoluble product is separated off by filtration, washed with 3 times 100 cm³ of water, 2 times 100 cm³ of diisopropyl ether and dried in air. 82.0 g of tert-butyl 2-[N-(3-methoxyphenyl)-2-phthalimidoacetamido]acetate, melting at 148° C., are thus obtained.

N-(3-Methoxyphenyl)-2-phthalimidoacetamide can be prepared as follows: 22.0 g of triethylamine are added to a solution of 26.0 g of 3-methoxyaniline in 200 cm³ of methylene chloride, followed by 48.0 g of 2-phthalimidoacetyl chloride in solution in 300 cm³ of methylene chloride, the temperature being maintained at about 20° C. The reaction mixture is stirred for 4 hours at this temperature and then 800 cm³ of water are added. The insoluble product is separated off by filtration, washed with 3 times 100 cm³ of water and dried in air. 65.0 g of N-(3-methoxyphenyl)-2-phthalimidoacetamide, melting at 171° C., are thus obtained.

2-Phthalimidoacetyl chloride can be prepared by the method described by W. Grassmann and E. Schulte-Uebbing, Chem. Ber., 83, 244–247, (1950).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Optically active hydroquinine 1-(3-aminophenyl) ethanesulphonate (Form A).

2. A process for preparing optically active hydroquinine 1-(3-aminophenyl)ethanesulphonate (Form A), which comprises the steps of:

a) acting an alkali metal sulphite on (RS)-1-(1-bromoethyl)-3-nitrobenzene in aqueous medium at a temperature ranging from 50° C. to 100° C. and converting the product of said acting to its potassium salt to obtain (RS)-potassium 1-(3-nitrophenyl)-ethanesulphonate.

b) converting (RS)-potassium 1-(3-nitrophenyl) ethanesulphonate to benzylquininium 1-(3-nitrophenyl)ethanesulphonate whose melting point is approximately 110° C. and the rotatory power $\alpha_D^{20}$ is −151.3° C.±1.5 (C=1.009%; methanol), by means of an N-benzylquininium halide, in the presence of potassium dihydrogenphosphate, in aqueous medium, at a temperature ranging from 10° C. to 30° C. and isolating, by recrystallization from 2-propanol, to produce form A benzylquininium 1-(3-nitrophenyl) ethanesulphonate.

c) reducing said form A benzylquininium 1-(3-nitrophenyl)ethanesulphonate obtained by b) by means of hydrogen under pressure, in the presence of a catalyst, at a temperature ranging from 10° C. to 30° C.

3. A process according to claim 2, wherein said acting of step a) is performed at a temperature of 80° C.

4. A process according to claim 2, wherein the product of said acting is recovered by converting said product into tetraalkylammonium salt or trialkylphenylalkylammonium salt and then converting said salt into potassium salt.

5. A process according to claim 2, wherein said process is carried out at a hydrogen pressure of 100 Kpa.

* * * * *